United States Patent
Chawla

(10) Patent No.: US 7,562,769 B2
(45) Date of Patent: Jul. 21, 2009

(54) FORMULATION AND PRESENTATION OF MEDICAMENTS

(75) Inventor: Brindra Paul Singh Chawla, West Bridgford Nottingham (GB)

(73) Assignee: Brintech International Limited, West Bridgford, Nottingham (GB)

( * ) Notice: Subject to any disclaimer, the term of this patent is extended or adjusted under 35 U.S.C. 154(b) by 214 days.

(21) Appl. No.: 10/548,790

(22) PCT Filed: Mar. 11, 2004

(86) PCT No.: PCT/GB2004/001031

§ 371 (c)(1), (2), (4) Date: Sep. 12, 2005

(87) PCT Pub. No.: WO2004/082557

PCT Pub. Date: Sep. 30, 2004

(65) Prior Publication Data

US 2006/0172009 A1 Aug. 3, 2006

(30) Foreign Application Priority Data

Mar. 15, 2003 (GB) ................................. 0305969.8
Mar. 15, 2003 (GB) ................................. 0305970.6

(51) Int. Cl.
*B65D 25/08* (2006.01)
*A61K 33/14* (2006.01)

(52) U.S. Cl. ...................... 206/219; 206/217; 206/528

(58) Field of Classification Search ................. 206/217, 206/219, 220, 568, 570, 528–540, 221, 438; 424/489, 680; 604/500

See application file for complete search history.

(56) References Cited

U.S. PATENT DOCUMENTS

| 2,470,296 | A | 5/1949 | Fields |
| 2,534,636 | A | 12/1950 | Stirn |
| 2,642,063 | A | 6/1953 | Brown |
| 3,155,573 | A | 11/1964 | Fowler |
| 3,669,113 | A | 6/1972 | Altounyan et al. |
| 3,899,121 | A | 8/1975 | Herbetko |
| 4,137,914 | A | 2/1979 | Wetterlin |
| 4,570,630 | A | 2/1986 | Elliott et al. |
| 4,841,964 | A | 6/1989 | Hurka et al. |

(Continued)

FOREIGN PATENT DOCUMENTS

DE 1039193 6/1955

(Continued)

*Primary Examiner*—J. Gregory Pickett
(74) *Attorney, Agent, or Firm*—Woodling, Krost and Rust

(57) ABSTRACT

A medicament package comprises a vessel adapted to hold a quantity of a liquid vehicle. The vessel has an opening formed therein. The opening engages a deformable enclosure which receives a medicament container that contains a unit dose of a medicament. The entire medicament package is sterile and is arranged such that by deformation of the enclosure the container may be dislodged from the enclosure into the vessel whereby the medicament may escape from the container and mix with the liquid vehicle. The medicament container is formed with one or more dispensing apertures through which the medicament may exit the container and/or liquid can enter the container. The medicament container may be formed as two or more components, the integrity of the container being maintained by its engagement with the enclosure and that integrity being lost once the container is released from the enclosure.

18 Claims, 3 Drawing Sheets

U.S. PATENT DOCUMENTS

| | | | |
|---|---|---|---|
| 4,860,740 A | 8/1989 | Kirk | |
| 5,286,864 A * | 2/1994 | Walther et al. | 546/137 |
| 5,415,162 A | 5/1995 | Casper | |
| 5,522,383 A | 6/1996 | Calvert et al. | |
| 5,524,613 A | 6/1996 | Haber et al. | |
| 5,562,918 A | 10/1996 | Stimpson | |
| 5,778,873 A | 7/1998 | Braithwaite | |
| 5,797,391 A | 8/1998 | Cook et al. | |
| 5,823,182 A | 10/1998 | Van Oort | |
| 5,873,360 A | 2/1999 | Davies | |
| 5,881,719 A | 3/1999 | Gottenauer et al. | |
| 5,896,855 A | 4/1999 | Hobbs et al. | |
| 6,089,227 A | 7/2000 | Nilsson | |
| 6,092,648 A | 7/2000 | Sellars | |
| 6,230,707 B1 | 5/2001 | Horlin | |
| 6,328,034 B1 | 12/2001 | Eisele et al. | |
| 6,418,926 B1 | 7/2002 | Chawla | |
| 6,520,179 B1 | 2/2003 | Von Schuckmann et al. | |
| 2002/0020636 A1 * | 2/2002 | Bergamini et al. | 206/219 |
| 2002/0065256 A1 | 5/2002 | Karlsson et al. | |
| 2005/0006273 A1 | 1/2005 | Chawla | |
| 2005/0115562 A1 | 6/2005 | Chawla | |

FOREIGN PATENT DOCUMENTS

| | | |
|---|---|---|
| DE | 1039193 | 9/1958 |
| EP | 0254394 | 1/1988 |
| EP | 0385156 | 9/1990 |
| EP | 0525720 A1 | 2/1993 |
| EP | 1016399 A2 | 7/2000 |
| EP | 1172122 A1 | 1/2002 |
| EP | 1 241 108 | 9/2002 |
| GB | 2264237 A | 2/1992 |
| GB | 2253200 | 9/1992 |
| WO | WO 91/19524 | 12/1991 |
| WO | WO 92/16249 | 10/1992 |
| WO | WO 94/19041 | 9/1994 |
| WO | WO 95/16483 | 6/1995 |
| WO | PCT/GB97/03478 | 6/1998 |
| WO | WO 98/26828 | 6/1998 |
| WO | WO 00/35522 | 6/2000 |
| WO | WO 02/085281 | 10/2002 |
| WO | WO 03/051439 | 6/2003 |
| WO | WO 03/051744 | 6/2003 |
| WO | WO 03/075988 | 9/2003 |

* cited by examiner

FORMULATION AND PRESENTATION OF MEDICAMENTS

This invention relates to improvements in the formulation and presentation of medicaments, and in particular to the formulation and packaging of medicaments that are administered in solution or suspension.

Many medicaments are necessarily or preferably administered in solution or suspension. Such solutions or suspensions may be administered using bottles, syringes, spray pumps or by any other suitable method. For convenience, such medicaments are generally packaged and sold as pre-prepared solutions or suspensions, many of which comprise sodium chloride in order to render them isotonic with body fluids.

However, certain medicaments are unstable when formulated as a solution or suspension. Such medicaments may degrade over time, with a loss of activity or even the generation of products that are not merely inactive, but harmful. In such cases, it is therefore necessary that the solution or suspension must be used within a short time of having been made up. The medicament may therefore be formulated in dry form, eg as a powder, and added to a measured volume of solvent by the patient immediately prior to administration. The medicament may, for instance, be packaged in a capsule or other container that is cut or ruptured and the medicament then added to the solvent and stirred, thereby forming the solution or suspension to be administered. Various delivery systems have also been proposed for such medicaments, in which the medicament, in dry form (eg a powder), is held separate from the solvent until it is desired to make up the solution or suspension (ie until just before use). Some form of barrier or membrane between the powder and the solvent is then broken, allowing the powder and the solvent to become mixed.

Disadvantages of medicament packaging of the type described above include the possibility of debris being produced when the capsule or container is cut or ruptured, or the membrane or barrier is broken, which may contaminate the medicament solution or suspension. In addition, the process of cutting or rupturing the capsule or container, adding the medicament to the solvent and then stirring is time consuming and may require considerable dexterity, particularly where the quantity of medicament is very small.

Furthermore, the process of filling the container with the desired dose of powdered medicament generally requires the use of a diluent, which is often present in an amount that considerably exceeds that of the active ingredient itself. Again, this is particularly the case where the quantity of medicament is very low, as for very potent medicaments. Diluents that are used are essentially inert materials such as lactose. Whilst such materials are normally not harmful, they do represent constituents of the pharmaceutical formulation that are of no benefit to the patient, and as such it would generally be desirable to omit them.

There have now been devised improvements in the formulation and presentation of medicaments that overcome or substantially mitigate the above-mentioned and/or other disadvantages associated with the prior art.

According to the invention, there is provided a medicament package comprising a vessel adapted to hold a quantity of a liquid vehicle, the vessel having an opening formed therein, to which opening is bonded a deformable enclosure, within which enclosure there is received a medicament container that contains a unit dose of a medicament, such that by deformation of the enclosure the container may be dislodged from the enclosure into the vessel, whereby the medicament may escape from the container and mix with the liquid vehicle.

The medicament package according to the invention is advantageous primarily in that the medicament can be stored within the package in isolation until the user wishes to prepare a solution or suspension for administration. The action of dispensing the medicament into the liquid vehicle is also very straightforward, requiring only finger pressure to be applied to the deformable enclosure, thereby allowing patients with limited dexterity to prepare the solution or suspension. The release of the medicament container from the enclosure does not involve the breaking or rupturing of the container or any membrane or barrier, and therefore does not lead to the generation of any debris that could be harmful to the patient (eg if inhaled). Furthermore, the container itself, when released from the enclosure into the vessel, may function as an agitator that promotes efficient mixing of the medicament and the liquid vehicle.

The medicament may escape from the medicament container by virtue of the latter being formed with one or more dispensing apertures, through which the medicament may exit the container and/or liquid can enter the container and flush out the contents of the container. Alternatively, the medicament container may be formed as two or more components, the integrity of the container being maintained by its engagement by the enclosure, and that integrity being lost once the container is released from the enclosure.

The vessel may take any suitable form. The vessel may, for instance, have the general form of a cup, a bottle or flask, or a syringe. The vessel may, where appropriate, be a part of a suitable delivery device, eg a nebuliser or a syringe.

The enclosure may be bonded to the body of the vessel, or may form part of a separate component, eg a cap or other closure, that engages the vessel, eg by a threaded connection.

The medicament package may be supplied with a suitable volume of liquid vehicle present in the vessel. Alternatively, the vessel may be charged with a suitable volume of liquid vehicle by the user immediately prior to use.

Following mixing of the medicament with the liquid vehicle contained within the vessel, the solution or suspension of medicament may be administered directly from the vessel. Alternatively, the solution or suspension may be transferred from the vessel to another container for administration. For example, the solution or suspension may be poured into a nebuliser or drawn up into a syringe.

In some embodiments, the enclosure is formed with one or more apertures, most commonly a single central aperture, that is closed, while the medicament container is held within the enclosure, by the medicament container. When the medicament container has been dislodged from the enclosure, that aperture then functions as an outlet by which the solution or suspension may be dispensed from the vessel. For example, the solution or suspension may be drawn up into a syringe via a needle or cannula inserted through the aperture, or expelled through the aperture by squeezing of the vessel (where the vessel, or a suitable part of the vessel) is of a flexible material). Where the aperture is relatively small, and the surface tension of the solution or suspension so permits, the solution or suspension may be dispensed from the vessel through the aperture drop-wise, simply by inverting the vessel and if necessary applying gentle squeezing and/or shaking. In a further embodiment of the invention, there is provided a second deformable element, which may be similar in form to the deformable enclosure (but which does not have an aperture). Depression of the second deformable element provides a pumping action by which the solution or suspension can be dispensed via the aperture in the first enclosure.

The deformable enclosure is preferably bonded to the periphery of the opening and extends therefrom such that the enclosure has the form of a cup and the opening constitutes an open mouth of the enclosure. In general, the shape of the cup will conform to that of the medicament container. Most preferably the enclosure fits closely around at least that part of the container which is formed with the dispensing aperture(s). The material of the enclosure may extend beyond the opening to which it is bonded, preferably with an inwardly extending lip to enhance the retention of the medicament container within the enclosure.

The arrangement is most preferably such that the medicament container is received by the enclosure with a close fit, and pressure applied, in use, by a user to the exterior of the enclosure deforms the enclosure and causes the container to be dispensed from the enclosure, through the open mouth thereof, and into the vessel.

The deformable enclosure may be bonded directly to the body of the vessel, or to the cap or other closure. Alternatively, the enclosure may be bonded to a rigid intermediate component in which the opening is formed, that is in turn connected to the body of the vessel (or cap etc), eg by means of an interference fit. The intermediate component may take the form of a support ring, with the deformable enclosure bonded to the interior of the support ring.

The intermediate component is preferably made of plastics material, and most preferably polypropylene. The deformable enclosure is preferably of elastomeric material. The elastomeric material is preferably water resistant and non-toxic. A particularly suitable elastomeric material is a medical grade thermoplastic rubber, eg that referred to as SANTO-PRENE (Advanced Elastomer Systems NV/SA, Leicester, United Kingdom).

The vessel, or at least the part of the vessel to which the enclosure is bonded, and the enclosure may be injection moulded in a two-step process. In such a process, the relevant part of the vessel is preferably injection moulded in a first step. The enclosure is then injection moulded onto the first moulding. The materials used for the relevant part of the vessel and the enclosure are preferably chosen such that they adhere when the second material is moulded onto the first. The preferred materials polypropylene and SANTOPRENE adhere in that fashion.

The medicament container preferably comprises two (or more) cooperating components, most preferably a cup and a closure which fit together. The cooperating components may fit together with a close, interference fit. In such a case, the enclosure will generally maintain its integrity when dislodged from the enclosure and is therefore provided with at least one opening through which the contents of the container can escape. Alternatively, the cooperating components may engage only loosely, being held together by virtue of being held in the enclosure, and may separate once released from the enclosure, thereby allowing the contents to escape. The container is preferably generally cylindrical, eg in the form of a drum. The medicament container is preferably made of plastics material of low moisture permeability and is most preferably made of high density polyethylene. The components of the medicament container are preferably injection moulded.

The entire medicament package according to the invention may be rendered sterile, eg by gamma-irradiation. Many embodiments of the invention will be completely closed systems, and in such embodiments release of the medicament container from the enclosure, and the consequent generation of the required solution or suspension, will occur without any loss of sterility.

Most preferably, the medicament container contains a unit dose of a pharmaceutical formulation comprising the unit dose of medicament in admixture with sodium chloride.

In another aspect, the invention provides a pharmaceutical formulation comprising a solid medicament intended for dissolution or dispersion in a liquid vehicle, the medicament being in admixture with sodium chloride. The formulation according to the invention is most preferably contained within the medicament container of the medicament package described above.

The formulation according to the invention is advantageous primarily in that it does not contain any excipient intended solely to act as a carrier to aid the handling and dosing of the active medicament. Instead, it is the sodium chloride, which is present in order to adjust the tonicity of the solution or suspension formed by dissolution or dispersion of the medicament, that also performs the function of a powder diluent.

The medicament and the sodium chloride are both present in the formulation in solid form. For example, both components may be present in particulate form, the formulation being prepared by simple admixture of particles of both materials. Alternatively, the formulation may comprise a solid body made up of both materials. Such a solid body may be prepared by compaction of a powder mixture of medicament and sodium chloride.

The proportions of medicament and sodium chloride in the formulation according to the invention may vary widely, but in general the sodium chloride will be present as the major constituent. In general, the formulation will comprise less than 50%, and more preferably less than 40%, less than 30%, less than 20%, or less than 10% w/w of medicament. In general, the formulation will comprise more than 50%, and more preferably more than 60%, more than 70%, more than 80% or more than 90% w/w of sodium chloride.

The formulation may further comprise one or more other excipients. Where present, such excipients will be present in relatively low amounts (eg less than 10%, more preferably less than 5% w/w in total). However, such other excipients will more commonly be formulated as part of the liquid vehicle with which the formulation is mixed prior to administration.

Most commonly, the required unit dose of medicament will be formulated with sufficient sodium chloride to yield an isotonic solution or suspension when the formulation is mixed with a given volume of liquid (normally water). The unit dose of medicament may be very low, eg of the order of micrograms. To achieve isotonicity, a concentration of sodium chloride of 0.9% w/v is required.

Thus, to achieve an isotonic solution with a volume of 5 cm$^3$, the required dose of medicament is formulated with 45 mg of sodium chloride. If the volume is to be 3 cm$^3$, then the quantity of sodium chloride required is 27 mg.

Bulk quantities of the formulation according to the invention may be prepared using essentially conventional techniques that will be familiar to those skilled in the art. Likewise, unit doses of the formulation may be filled into suitable containers by known techniques, similar to techniques that are conventionally used for the filling of powder mixtures (eg mixtures of medicament and lactose) into capsules or the like.

The unit dose of the formulation, filled into a suitable container, may if necessary or desired be rendered sterile, eg by gamma-irradiation. The unit dose of the formulation may be supplied with a vessel containing the required quantity of liquid vehicle, which may further comprise other excipients (eg surfactant, etc). Alternatively, the patient may himself measure the required quantity of liquid and add the unit dose of powder to it, immediately prior to use.

According to another aspect of the invention, there is provided the use of sodium chloride as a diluent for a medicament in solid form that is intended for dissolution or dispersion in a liquid vehicle prior to administration.

The invention further provides a process for the preparation of a pharmaceutical formulation, which process comprises admixing a medicament in solid form with particulate sodium chloride.

It will be understood that all references to a medicament as used herein encompass the use of two or more different medicaments in admixture.

Examples of medicaments that may be formulated in accordance with the invention include drugs intended for administration by inhalation. Such drugs include
 a) bronchodilators ($\beta_2$-agonists), eg fenoterol, formoterol, salmeterol and salbutamol;
 b) steroids, eg budesonide, fluticasone and triamcinolone acetonide;
 c) anticholinergic agents, eg ipratropium bromide and oxitropium bromide;
 d) antiallergic agents, eg sodium cromoglycate and nedocromil sodium;
 e) antibiotics, eg tobramycin;
 f) proteins and peptides, eg insulin;
 g) mucolytics; and
 h) vaccines.

Mixtures of medicaments that may be used include mixtures of:
 a) bronchodilators ($\beta_2$-agonists) and steroids, eg
  formoterol and budesonide,
  salmeterol and fluticasone,
  formoterol and fluticasone,
  salmeterol and budesonide;
 b) anticholinergics and steroids, eg
  ipratropium bromide and budesonide,
  ipratropium bromide and fluticasone,
  oxitropium bromide and budesonide,
  oxitropium bromide and fluticasone; and
 c) antiallergic agents and steroids or anti-cholinergics, eg
  sodium cromoglycate and budesonide,
  sodium cromoglycate and fluticasone,
  sodium cromoglycate and ipratropium bromide,
  sodium cromoglycate and oxitropium bromide,
  nedocromil sodium and budesonide,
  nedocromil sodium and fluticasone,
  nedocromil sodium and ipratropium bromide;
  nedocromil sodium and oxitropium bromide.

The invention will now be described in greater detail, by way of illustration only, with reference to the accompanying drawings, in which FIG. 1 is a side view of a first embodiment of a medicament package according to the invention;

Figure 1:
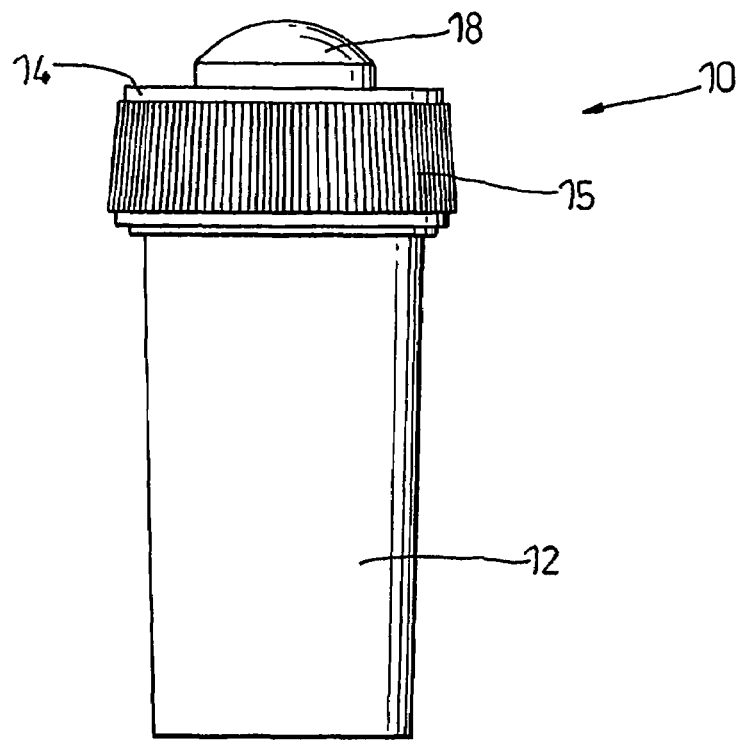
Figure 2:
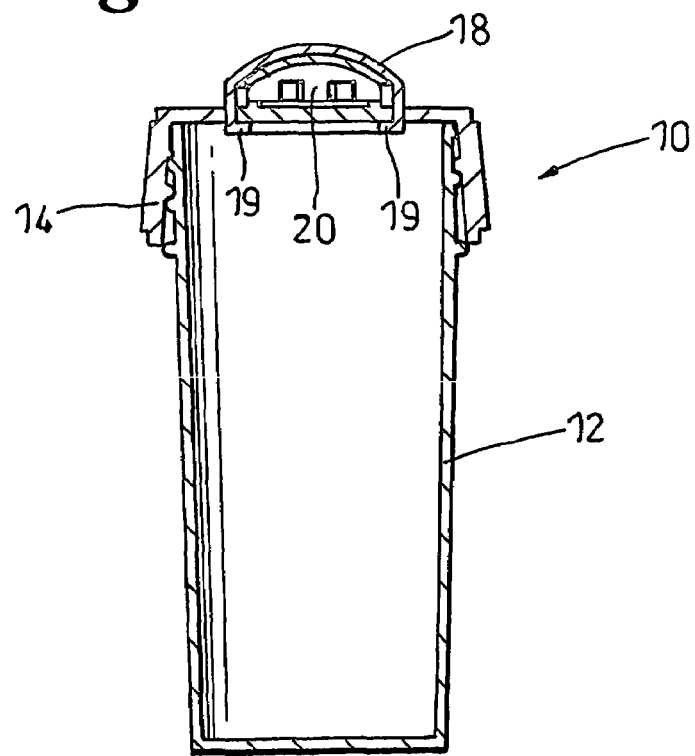
FIG. 2 is a diametrical section of the medicament package of FIG. 1.

A first embodiment of a medicament package according to the invention is shown in FIGS. 1 and 2 and is generally designated 10. The medicament package 10 comprises a vessel 12 and a cap 14. The vessel 12 is formed in a rigid plastics material and the cap 14 is formed in polypropylene.

The vessel 12 is generally cylindrical with a closed lower end and an open upper end (as viewed in FIGS. 1 and 2). The diameter of the vessel 12 gradually increases from the lower to the upper end. The lower surface of the vessel 12 is flat so that the medicament package 10 may rest on a substantially flat surface in an upright position.

The upper end of the vessel 12 is formed with an external thread for engagement with the cap 14, which in turn is formed with an internally-threaded downwardly-depending circumferential skirt. The external surface of the cap 14 is formed with vertical ribs, which constitute a grip 15 that facilitates application and removal of the cap 14 from the vessel 12. The cap 14 has a circular aperture at its centre, to the periphery of which is bonded a deformable enclosure 18.

The deformable enclosure 18 is generally cylindrical, with a dome-shaped upper part. The open lower end of the enclosure 18 is formed with an inwardly extending lip 19. The deformable enclosure 18 holds a medicament container 20 (shown in more detail in FIGS. 3 and 4) which fits closely within the enclosure 18 with the lip 19 lying alongside the lower surface of the container 20.

The deformable enclosure 18 is formed in an elastomeric material. A suitable elastomeric material is medical grade Santoprene thermoplastic rubber from Advanced Elastomer Systems.

Figure 3:
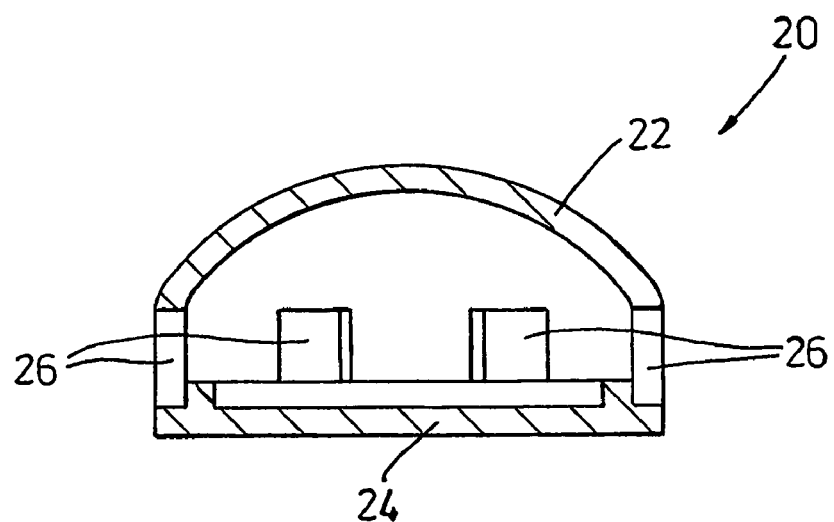
FIG. 3 is diametrical section of a medicament container which forms part of the medicament package according to the invention.
Figure 4:
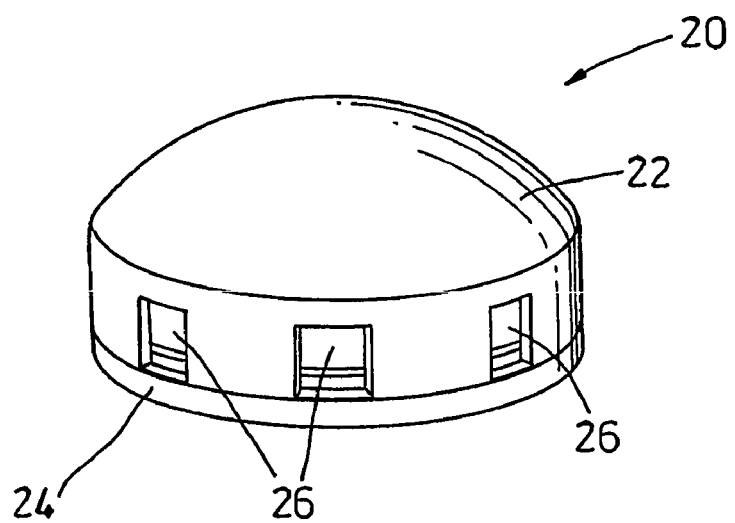
FIG. 4 is a perspective view of the medicament container of FIG. 4.

The medicament container 20 is shown in more detail in FIGS. 3 and 4. The medicament container 20 comprises an inverted cup 22 and a closure 24, both of plastics material. The cup 22 conforms in shape to the interior of the enclosure 18, comprising a cylindrical main body and a closed upper end that is of generally domed shape.

The cylindrical main body of the cup 22 is formed with a series of equiangularly spaced rectangular openings 26 which extend upwardly from the open end of the cup 22 along the majority of the height of the main body.

The closure 24 comprises a disc with a diameter identical to the external diameter of the cup 22 and an upstanding rim that is received closely within the lower end of the cup 22 with an interference fit. The rim extends upwardly to occlude the lower part of each opening 26 in the cup 22, as shown in FIG. 4. The container 20 is dimensioned so that the container 20 is closely received with an interference fit within the enclosure 18 and the lip 19 lies alongside the lower surface of the container 20.

The vessel 12, cap 14 and deformable enclosure 18 are formed by injection-moulding. The cap 14 and deformable enclosure 18 are formed in a two-shot injection moulding process in which elastomeric material, which forms the deformable enclosure 18, is injection-moulded onto a previously injection-moulded cap 14, thereby bonding the deformable enclosure 18 to the cap 14.

The medicament package is assembled by filling a unit dose of medicament into the cup 22 (normally with the latter in an inverted condition), and then applying the closure 24 to the open mouth of the cup 22. The assembled medicament container 20 is then pressed into the enclosure 18. Alternatively, the cup 22 may be inserted into the enclosure 18, the cup 22 then filled with the dose of medicament and the closure 24 then applied to the open mouth of the cup 22. The latter approach may also be used for embodiments of the invention in which the components of the container are not fixed together, but which separate after release from the enclosure, rather than having dispensing apertures 26. Finally, the cap 14 is threadedly engaged with the vessel 12. The vessel may be filled with a quantity of liquid (most commonly water, or an aqueous solution) before the cap 14 is fitted. Alternatively, the package may be supplied without any liquid present in the vessel, the cap 14 being removed and liquid introduced by the user prior to use of the package.

In use, medicament is contained within the medicament container 20 and the apertures 26 of the container 20 are sealed by the deformable enclosure 18, thereby preventing escape of the medicament from the container 20. The vessel 12 is either pre-charged with the liquid vehicle or liquid is introduced into the vessel 12, immediately prior to administration, by temporarily disengaging the cap 14 from the enclosure 18. The liquid contained within the enclosure 18 is prevented from coming into contact with the medicament by the close fit between the deformable enclosure 18 and the container 20.

In order to prepare the solution or suspension for administration, the medicament is introduced into the liquid contained within the vessel 12 by applying downward finger pressure on the deformable enclosure 18, thereby causing the container 20 to be displaced from the enclosure 18 and to fall into the liquid. When the container 20 is released from the enclosure 18 the openings 26 are exposed, and consequently the medicament can escape from the container 20 via the openings 26. The liquid may also flow into the container 20 and flush the medicament out of the container 20. The process of dispersion and/or dissolution of the medicament in the liquid may be facilitated by shaking of the vessel 12, in which case the container 20 may itself act as a mechanical agitator.

After mixing of the medicament and liquid, the prepared solution or suspension may then be dispensed from the medicament package 10 by removing the cap 14 and pouring the solution or suspension into a suitable administration device, eg a nebuliser. It will be appreciated that in other embodiments the vessel may actually form part of such a device (or may be fitted into such a device) and will be provided with means enabling the direct administration of the solution or suspension from the vessel.

Figure 5:
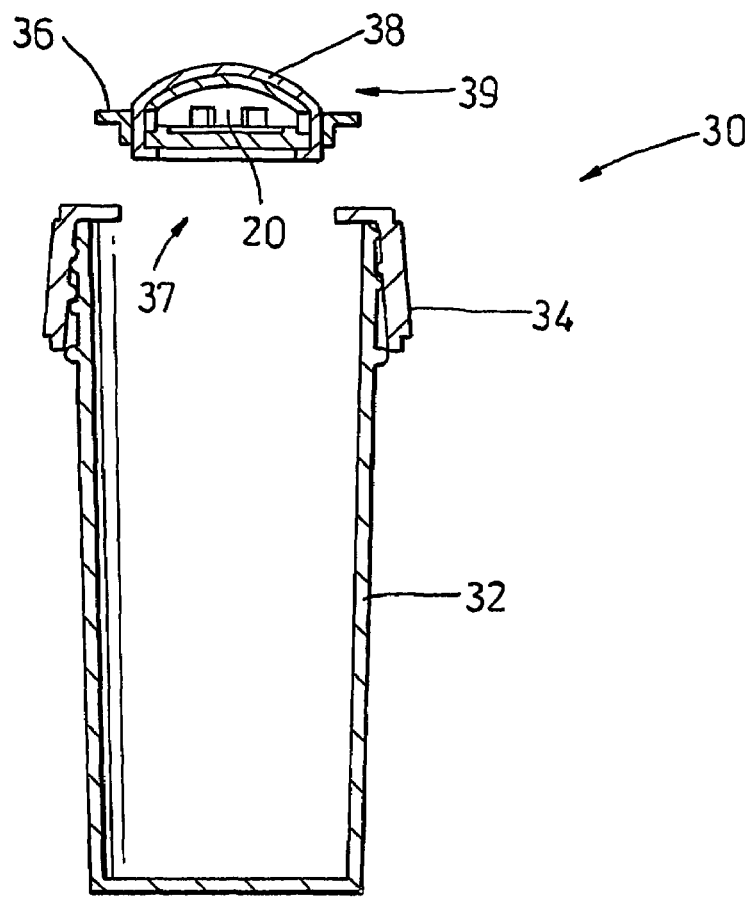
FIG. 5 is a diametrical section of a second embodiment of a medicament package according to the invention.
Figure 6:
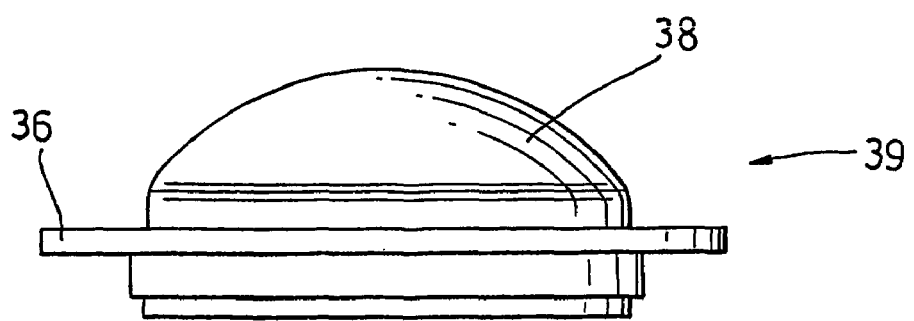
FIG. 6 is a side view of a support ring and deformable enclosure which form part of the medicament package of FIG. 5.

Turning now to FIGS. 5 and 6, a second embodiment of a medicament package according to the invention is shown and generally designated 30. The second embodiment 30 is similar to the first embodiment 10, in that it comprises a vessel 32, a cap 34 and a deformable enclosure 38. However, the deformable enclosure 38 is bonded, not directly to the cap 34, but to a support ring 36 to form a dosing assembly (generally designated 39) that may be separated from the cap 34, as shown in FIG. 5. As with the first embodiment 10, a medicament container 20 is closely received, with an interference fit, within the deformable enclosure 38.

The deformable enclosure 38 and support ring 36 are formed by a two-shot injection moulding process as described above in respect of the deformable enclosure 18 and cap 14 of the first embodiment 10.

The support ring 36 is of L-shaped cross-section, comprising a cylindrical ring with an outwardly extending flange, as shown more clearly in FIG. 6. The external surface of the ring fits closely, with an interference fit, within a corresponding circular aperture 37 in the centre of the upper surface of the cap 34.

In use, liquid is introduced into the vessel 32. This may be done by removing the cap 34 from the vessel 32, or alternatively via the circular aperture 37 with the dosing assembly 39 removed. In the latter case, a dosing assembly 39 is then positioned, with an interference fit, within the aperture 37 of the cap 14. Otherwise, the cap 34, with the dosing assembly 39 in place, is engaged with the vessel 32. As with the first embodiment 10, the liquid contained within the vessel 32 is prevented from coming into contact with the medicament by the close fit between the deformable enclosure 38 and the container 20.

As for the first embodiment, in order to prepare the solution or suspension, the medicament is introduced into the liquid by applying downward pressure on the deformable enclosure 18, thereby causing the container 20 to fall into the liquid.

After use, the dosing assembly 39 may be removed from the aperture 37 of the cap 34, and replaced by another. The medicament package 30 may then be re-used, as described above, with a dosing assembly 39 containing a new medicament container 20.

The following Examples illustrate unit doses of medicament that may be contained within the medicament container 20.

EXAMPLE 1

| | |
|---|---|
| Sodium cromoglycate | 20 mg |
| Sodium chloride | 45 mg |

The unit dose having the above composition is intended for dissolution in 5 ml of water, resulting in an isotonic solution of sodium cromoglycate.

EXAMPLE 2

| | |
|---|---|
| Salbutamol | 100 µg |
| Sodium chloride | 18 mg |

The unit dose having the above composition is intended for dissolution in 2 ml of water, resulting in an isotonic solution of salbutamol.

EXAMPLE 3

| | |
|---|---|
| Budesonide | 200 µg |
| Formoterol | 4.5 µg |
| Sodium Chloride | 27 mg |

The unit dose having the above composition is intended for dissolution in 3 ml of water, resulting in an isotonic solution of the two active ingredients.

The invention claimed is:

1. A medicament package comprising:
   a vessel adapted to hold a quantity of a liquid vehicle, said vessel includes a body having an interior and an exterior, and said vessel having an opening formed therein;
   a deformable enclosure, said deformable enclosure includes an exterior and an interior;
   said deformable enclosure includes a lip and a cup-shaped portion;
   said deformable enclosure engages said opening in said vessel;
   a medicament container;
   said medicament container includes an aperture for communicating medicament therethrough;

said medicament package being sterile;
said medicament container includes a unit dose of medicament;
said medicament container includes a cup-shaped portion;
said medicament container moves between a first and second position;
said medicament container resides in said first position within said deformable enclosure supported by said lip of said deformable enclosure and interfitting said cup-shaped portion of said deformable enclosure;
said medicament container moves from said first position under pressure applied from said exterior of said deformable enclosure toward said interior of said deformable enclosure to said second position within said interior of said vessel; and,
and said medicament escapes through said aperture of said medicament container into said liquid vehicle mixing with said liquid vehicle when said medicament container is in said second position.

2. A medicament package as claimed in claim 1, wherein said medicament container includes two components, said container engaging said deformable enclosure maintaining its integrity, and, said integrity being lost once said medicament container is forced from said enclosure and moves to said second position within said vessel.

3. A medicament package as claimed in claim 1 wherein said medicament container engages said deformable enclosure, said aperture in said medicament container is closed and sealed while said medicament container engages and is held within said deformable enclosure in said first position, and, said aperture opens when said medicament container is dislodged from said enclosure and resides in said second position.

4. A medicament package as claimed claim 1 wherein said deformable enclosure is bonded to said periphery of said opening of said vessel and extends therefrom such that said enclosure includes said cup-shaped portion and said opening constitutes an open mouth of the enclosure.

5. A medicament package as claimed in claim 4 wherein said medicament container includes a plurality of dispensing apertures, and said deformable enclosure seals said dispensing apertures.

6. A medicament package as claimed in claim 5 wherein said medicament container is received within said deformable enclosure and pressure applied to said exterior of said deformable enclosure deforms said enclosure and causes said container to be expelled from said enclosure through said open mouth thereof and into said second position in said interior of said vessel.

7. A medicament package as claimed claim 1 wherein said deformable enclosure is bonded to said body of said vessel.

8. A medicament package as claimed in claim 1 wherein said deformable enclosure is an elastomeric material.

9. A medicament package as claimed in claim 1 wherein said vessel and said deformable enclosure are injection molded in a two-step process in which said vessel is injection molded first and said enclosure is then injection molded onto said first moulding.

10. A medicament package as claimed in claim 1 wherein said medicament container contains a unit dose of a pharmaceutical formulation and the unit dose of medicament is in admixture with sodium chloride.

11. A medicament package as claimed in claim 10 wherein said medicament and said sodium chloride are both present in the formulation in particulate form.

12. A medicament package as claimed in claim 10 wherein said formulation comprises a solid body made up of said medicament and sodium chloride.

13. A medicament package as claimed in claim 12 wherein said solid body is prepared by compaction of a powder mixture of medicament and sodium chloride.

14. A medicament package as claimed in claim 10 wherein said formulation comprises less than 50% w/w of medicament.

15. A medicament package as claimed in claim 10 wherein said formulation comprises more than 50% w/w of sodium chloride.

16. A medicament package as claimed in claim 10 wherein said unit dose of medicament is formulated with sufficient sodium chloride to yield an isotonic solution or suspension when said formulation is mixed with a given volume of liquid.

17. A medicament package comprising:
a vessel adapted to hold a quantity of a liquid vehicle, said vessel includes a body having an interior and an exterior, and said vessel having an opening formed therein;
an inwardly deformable bulbous enclosure, said inwardly deformable bulbous enclosure includes an exterior and an interior;
said inwardly deformable bulbous enclosure includes a lip, a cup-shaped portion and an open mouth;
said inwardly deformable bulbous enclosure engages said opening in said vessel;
a medicament container;
said medicament container includes an interior and an exterior;
said exterior of said medicament container is generally conjugately shaped with respect to said interior of said inwardly deformable bulbous enclosure;
said medicament container includes apertures for communicating medicament therethrough;
said medicament package being sterile;
said medicament container includes a unit dose of medicament;
said medicament container includes a cup-shaped portion;
said medicament container moves between a first and second position;
said exterior of said medicament container resides in said first position within said inwardly deformable bulbous enclosure supported by said lip of said inwardly deformable enclosure and interfitting said cup-shaped portion of said interior of said inwardly deformable enclosure;
said exterior of said medicament container in said first position sealingly engages said inwardly deformable bulbous enclosure sealing said apertures prohibiting communication of said medicament therethrough;
said medicament container forcibly moves from said first position through said open mouth of said inwardly deformable bulbous enclosure and into said second position within said interior of said vessel under pressure applied from said exterior of said inwardly deformable enclosure toward said interior of said inwardly deformable enclosure; and,
said medicament escapes through said aperture of said medicament container into said liquid vehicle mixing with said liquid vehicle when said medicament container is in said second position.

18. A medicament package comprising:
a vessel adapted to hold a quantity of a liquid vehicle, said vessel includes a body having an interior and an exterior, and said vessel having an opening formed therein;

an inwardly deformable bulbous enclosure, said inwardly deformable bulbous enclosure includes an exterior and an interior;
said inwardly deformable bulbous enclosure includes a lip, a cup-shaped portion and an open mouth;
a support ring;
said support ring includes an interior portion;
said support ring is affixed to said vessel;
said deformable enclosure is bonded to said interior of said support ring;
a medicament container;
said medicament container includes an interior and an exterior;
said exterior of said medicament container is substantially conjugately shaped with respect to said interior of said deformable bulbous enclosure;
said medicament container includes apertures for communicating medicament therethrough;
said medicament package being sterile;
said medicament container includes a unit dose of medicament;
said medicament container includes a cup-shaped portion;
said medicament container moves between a first and second position;
said exterior of said medicament container resides in said first position within said inwardly deformable bulbous enclosure supported by said lip of said inwardly deformable enclosure and interfitting said cup-shaped portion of said interior of said inwardly deformable enclosure;
said exterior of said medicament container in said first position sealingly engages said inwardly deformable bulbous enclosure sealing said apertures prohibiting communication of said medicament therethrough;
said medicament container forcibly moves from said first position through said open mouth of said inwardly deformable bulbous enclosure and into said second position within said interior of said vessel under pressure applied from said exterior of said inwardly deformable enclosure toward said interior of said inwardly deformable enclosure; and,
said medicament escapes through said aperture of said medicament container into said liquid vehicle mixing with said liquid vehicle when said medicament container is in said second position.

* * * * *